United States Patent
Shlenker et al.

[11] Patent Number: 5,965,276
[45] Date of Patent: *Oct. 12, 1999

[54] METHOD OF FORMING A MEMBRANE ESPECIALLY A LATEX OR POLYMER MEMBRANE INCLUDING MULTIPLE DISCRETE LAYERS

[75] Inventors: Robin Renee Thill Shlenker, Malibu, Calif.; David J. Lester, Littleton; Clive C. Solomons, Denver, both of Colo.; Sebastian S. Plamthottam, Upland, Calif.

[73] Assignee: BIO Barrier, Inc., Los Angeles, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/917,050

[22] Filed: Aug. 13, 1997

Related U.S. Application Data

[63] Continuation of application No. 08/476,843, Jun. 7, 1995, Pat. No. 5,679,399, which is a continuation-in-part of application No. 08/291,002, Aug. 15, 1994, Pat. No. 5,549,924, which is a continuation-in-part of application No. 07/976,881, Nov. 16, 1992, Pat. No. 5,338,565, which is a continuation of application No. 07/825,546, Jan. 24, 1992, Pat. No. 5,165,953, which is a continuation-in-part of application No. 07/536,772, Jun. 12, 1990, Pat. No. 5,130,159, which is a continuation-in-part of application No. 07/536,773, Jun. 12, 1990, Pat. No. 5,128,168, which is a continuation-in-part of application No. 07/482,978, Feb. 22, 1990, Pat. No. 5,045,341, which is a continuation-in-part of application No. 07/246,337, Sep. 19, 1988, Pat. No. 4,935,260, which is a continuation-in-part of application No. 07/143,184, Jan. 13, 1988, Pat. No. 4,919,966, which is a continuation-in-part of application No. 07/074,629, Jul. 17, 1987, Pat. No. 4,771,482.

[51] Int. Cl.⁶ .............................. B32B 7/00; B32B 9/00; A61F 6/00; A61D 19/00
[52] U.S. Cl. ............................... 428/492; 2/161.7; 2/168; 215/11.1; 424/411; 424/424; 424/432; 424/485; 428/36.8; 428/36.91; 428/320.2; 428/321.1; 604/264; 604/265; 604/289; 604/292; 604/304; 604/329; 604/338; 604/349; 128/837; 128/844
[58] Field of Search .................... 2/168, 161.7; 128/844, 128/837; 424/404, 411, 424, 432, 485; 427/2.3, 407.1; 215/11.1; 428/36.8, 36.91, 320.2, 321.1, 492; 604/264, 265, 289, 292, 304, 327, 338, 349

[56] References Cited

U.S. PATENT DOCUMENTS

D. 300,463   3/1989   Nemec et al. ............. Chamberlain .

(List continued on next page.)

FOREIGN PATENT DOCUMENTS 624862   8/1989   Australia .   ...................... Australia .

(List continued on next page.)

OTHER PUBLICATIONS

Article re A Method for Hydron Impregnation of Silicone Rubber by P. Predecki, J. Biomed. Mater. Res. vol. 8 (1974) pp. 487–489.

*Primary Examiner*—Diana Dudash

[57] ABSTRACT

Single and multiple layer membranes such as gloves and condoms include one or more deactivating barrier layers and/or indicating layers to indicate to a user membrane breach or the presence of a harmful substance in blood or body fluids. A membrane may include one or more permeable or semipermeable layers to disperse contained substances such as lubricants, biocides, spermicides, or indicators outwardly, and may also include permeable or semipermeable layers to allow transmission of body fluids or other environmental fluids inwardly into contact with an indicating or treating substance. An intermediate layer of a multi-layer membrane may include a substance to wipe, cleanse, sterilize, or otherwise treat a piercing needle. A membrane may include a sealing or coating to entrap indicators or other agents such as biocides therein. A method of making membranes such as gloves results in a double glove having discrete inner or outer layers joined only in a cuff region. Admixing of gentian violet with latex prior to membrane formation provides biocidal properties, anti-aging effects prolonging shelf-life and tear resistance, and reduces allergic reactions in latex-allergic users.

14 Claims, 2 Drawing Sheets

U.S. PATENT DOCUMENTS

| | | |
|---|---|---|
| 540,241 | 10/1895 | Chamberlain |
| 1,954,262 | 4/1934 | Potter . |
| 2,410,460 | 11/1946 | Robinson . |
| 2,586,674 | 2/1952 | Lonne . |
| 2,792,835 | 5/1957 | Ferguson . |
| 3,079,351 | 2/1963 | Staneslow . |
| 3,110,035 | 11/1963 | LaHue . |
| 3,121,877 | 2/1964 | Gintner . |
| 3,342,182 | 9/1967 | Charos . |
| 3,384,083 | 5/1968 | Cozza et al. . |
| 3,390,214 | 6/1968 | Woods . |
| 3,496,938 | 2/1970 | Furuse et al. . |
| 3,633,216 | 1/1972 | Schonholtz . |
| 3,672,351 | 6/1972 | Ubersax . |
| 3,710,795 | 1/1973 | Higuchi et al. . |
| 3,859,410 | 1/1975 | Sidley ............ 264/303 |
| 3,911,501 | 10/1975 | Seltzer . |
| 3,971,499 | 7/1976 | Goodrich, Jr. et al. . |
| 3,975,775 | 8/1976 | Alsop . |
| 4,062,834 | 12/1977 | Gilding et al. . |
| 4,112,138 | 9/1978 | Davis et al. . |
| 4,185,330 | 1/1980 | Stager . |
| 4,190,721 | 2/1980 | Hertel ............ 528/486 |
| 4,214,321 | 7/1980 | Nuwayser . |
| 4,286,592 | 9/1981 | Chandrasekaran . |
| 4,286,593 | 9/1981 | Place et al. . |
| 4,302,852 | 12/1981 | Joung . |
| 4,332,243 | 6/1982 | Gutnick . |
| 4,377,567 | 3/1983 | Geho . |
| 4,404,197 | 9/1983 | Fox, Jr. et al. . |
| 4,413,423 | 11/1983 | Sternlieb . |
| 4,415,548 | 11/1983 | Reddy . |
| 4,427,003 | 1/1984 | Fennimore et al. . |
| 4,432,357 | 2/1984 | Pomeranz . |
| 4,438,177 | 3/1984 | Potter et al. . |
| 4,446,124 | 5/1984 | Fox, Jr. et al. . |
| 4,446,860 | 5/1984 | Gutnick . |
| 4,471,538 | 9/1984 | Pomeranz et al. . |
| 4,499,154 | 2/1985 | James et al. . |
| 4,512,337 | 4/1985 | Leveskis . |
| 4,522,819 | 6/1985 | Fox, Jr. et al. . |
| 4,534,078 | 8/1985 | Viesturs et al. . |
| 4,535,078 | 8/1985 | Fox, Jr. et al. . |
| 4,545,841 | 10/1985 | Jackrel . |
| 4,559,223 | 12/1985 | Fox, Jr. . |
| 4,563,485 | 1/1986 | Fox, Jr. et al. . |
| 4,581,028 | 4/1986 | Fox, Jr. et al. . |
| 4,592,920 | 6/1986 | Murtfeldt . |
| 4,595,001 | 6/1986 | Potter et al. . |
| 4,655,202 | 4/1987 | Potter et al. . |
| 4,657,006 | 4/1987 | Rawlings et al. . |
| 4,662,006 | 5/1987 | Ross, Jr. . |
| 4,672,956 | 6/1987 | Potter et al. . |
| 4,675,347 | 6/1987 | Mochizuki et al. . |
| 4,696,065 | 9/1987 | Elenteny . |
| 4,704,130 | 11/1987 | Gilding et al. . |
| 4,747,401 | 5/1988 | Potter et al. . |
| 4,771,482 | 9/1988 | Shlenker . |
| 4,798,201 | 1/1989 | Rawlings et al. . |
| 4,813,966 | 3/1989 | Gilding et al. . |
| 4,851,266 | 7/1989 | Momose et al. . |
| 4,853,978 | 8/1989 | Stockum . |
| 4,867,968 | 9/1989 | Allen . |
| 4,873,998 | 10/1989 | Joyner ............ 128/879 |
| 4,876,293 | 10/1989 | Durney et al. . |
| 4,881,277 | 11/1989 | Hogle . |
| 4,888,007 | 12/1989 | Loeb et al. . |
| 4,901,372 | 2/1990 | Pierce . |
| 4,919,966 | 4/1990 | Shlenker . |
| 4,930,522 | 6/1990 | Busnel et al. . |
| 4,935,260 | 6/1990 | Shlenker . |
| 4,935,308 | 6/1990 | Guerra et al. . |
| 4,977,903 | 12/1990 | Haines . |
| 4,988,296 | 1/1991 | Spencer ............ 438/163 |
| 4,995,119 | 2/1991 | Codkind . |
| 5,001,354 | 3/1991 | Gould et al. ............ 250/516.1 |
| 5,008,110 | 4/1991 | Benecke et al. . |
| 5,010,883 | 4/1991 | Rawlings et al. . |
| 5,017,427 | 5/1991 | Machida et al. . |
| 5,019,096 | 5/1991 | Fox Jr. et al. . |
| 5,020,162 | 6/1991 | Kersten et al. . |
| 5,024,852 | 6/1991 | Busnel et al. . |
| 5,031,245 | 7/1991 | Milner . |
| 5,033,115 | 7/1991 | Bowling et al. ............ 2/51 |
| 5,045,341 | 9/1991 | Shlenker . |
| 5,071,656 | 12/1991 | Lee et al. . |
| 5,073,365 | 12/1991 | Katz et al. . |
| 5,080,646 | 1/1992 | Theeuwes et al. . |
| 5,084,514 | 1/1992 | Szczechura et al. . |
| 5,087,240 | 2/1992 | Sibalis . |
| 5,089,205 | 2/1992 | Huang et al. . |
| 5,091,442 | 2/1992 | Milner . |
| 5,108,710 | 4/1992 | Little et al. . |
| 5,115,805 | 5/1992 | Bommannan et al. . |
| 5,122,116 | 6/1992 | Kriesel et al. . |
| 5,128,168 | 7/1992 | Shlenker et al. . |
| 5,130,159 | 7/1992 | Shlenker et al. . |
| 5,133,087 | 7/1992 | Machida et al. . |
| 5,133,090 | 7/1992 | Modak et al. . |
| 5,138,719 | 8/1992 | Orlianges et al. . |
| 5,141,748 | 8/1992 | Rizzo . |
| 5,141,750 | 8/1992 | Lee et al. . |
| 5,147,296 | 9/1992 | Theeuwes et al. . |
| 5,156,949 | 10/1992 | Luciw et al. . |
| 5,160,316 | 11/1992 | Henley . |
| 5,163,899 | 11/1992 | Sibalis . |
| 5,164,189 | 11/1992 | Farhadich et al. . |
| 5,165,953 | 11/1992 | Shlenker et al. . |
| 5,169,382 | 12/1992 | Theeuwes et al. . |
| 5,169,383 | 12/1992 | Gyory et al. . |
| 5,175,003 | 12/1992 | Goldman . |
| 5,181,276 | 1/1993 | Kersten et al. . |
| 5,191,902 | 3/1993 | Wilk . |
| 5,223,262 | 6/1993 | Kim et al. . |
| 5,224,221 | 7/1993 | Richardson et al. . |
| 5,224,373 | 7/1993 | Williams et al. . |
| 5,230,896 | 7/1993 | Yeh et al. . |
| 5,231,975 | 8/1993 | Bommannan et al. . |
| 5,232,438 | 8/1993 | Theeuwes et al. . |
| 5,234,690 | 8/1993 | Chiang et al. . |
| 5,234,957 | 8/1993 | Mantelle . |
| 5,250,028 | 10/1993 | Theeuwes et al. . |
| 5,260,069 | 11/1993 | Chen . |
| 5,262,165 | 11/1993 | Govil et al. . |
| 5,266,325 | 11/1993 | Kuzma et al. . |
| 5,267,957 | 12/1993 | Kriesel et al. . |
| 5,273,755 | 12/1993 | Venktrama et al. . |
| 5,273,756 | 12/1993 | Fallon et al. . |
| 5,273,757 | 12/1993 | Jaeger et al. . |
| 5,284,159 | 2/1994 | Wilk . |
| 5,284,660 | 2/1994 | Lee et al. . |
| 5,290,561 | 3/1994 | Farhadieh et al. . |
| 5,292,515 | 3/1994 | Moro et al. . |
| 5,293,648 | 3/1994 | Finley . |
| 5,306,250 | 4/1994 | March et al. . |
| 5,317,759 | 6/1994 | Pierce . |
| 5,317,760 | 6/1994 | Best . |
| 5,335,373 | 8/1994 | Dangman et al. . |
| 5,338,565 | 8/1994 | Shlenker et al. . |
| 5,357,636 | 10/1994 | Dresdner, Jr. et al. . |
| 5,411,034 | 5/1995 | Beck et al. . |

| | | |
|---|---|---|
| 5,459,879 | 10/1995 | Fuchs . |
| 5,483,697 | 1/1996 | Fuchs . |
| 5,486,322 | 1/1996 | Fuchs ................................... 264/46.5 |
| 5,674,399 | 10/1997 | Shlenker et al. ................ 427/407.1 X |

FOREIGN PATENT DOCUMENTS

| | | |
|---|---|---|
| 620913 | 9/1989 | |
| 654162 | 12/1991 | Australia . |
| 2058210 | 2/1995 | Canada . |
| 0141628 | 10/1984 | European Pat. Off. . |
| 0147970 | 12/1984 | European Pat. Off. . |
| 0229862 | 1/1986 | European Pat. Off. . |
| 0287204 | 2/1988 | European Pat. Off. . |
| 0299802 | 7/1988 | European Pat. Off. . |
| 0306389 | 8/1988 | European Pat. Off. . |
| 328421 | 2/1989 | European Pat. Off. . |
| 0368456 | 9/1989 | European Pat. Off. . |
| 0427997 | 10/1990 | European Pat. Off. . |
| 0443870 | 2/1991 | European Pat. Off. . |
| 645128A1 | 9/1994 | European Pat. Off. . |
| 0672509A2 | 3/1995 | European Pat. Off. . |
| 2623087 | 3/1987 | France . |
| 2663035 | 6/1990 | France . |
| 0442551 | 4/1927 | Germany . |
| 1917699 | 4/1969 | Germany . |
| 3411957 | 3/1984 | Germany . |
| 3411957 | 10/1984 | Germany . |
| 540241 | 10/1941 | United Kingdom . |
| 2104087 | 7/1982 | United Kingdom . |
| 2287427 | 3/1994 | United Kingdom . |
| 8501208 | 3/1985 | WIPO . |
| 8904647 | 6/1989 | WIPO . |
| 9001956 | 3/1990 | WIPO . |

METHOD OF FORMING A MEMBRANE ESPECIALLY A LATEX OR POLYMER MEMBRANE INCLUDING MULTIPLE DISCRETE LAYERS

CROSS-REFERENCE TO RELATED APPLICATIONS

This application is a continuation of application Ser. No. 08/476,843 filed Jun. 7, 1995 which application is now allowed and which is now U.S. Pat. No. 5,679,399, patented Oct. 21, 1997 which is a continuation-in-part of U.S. patent application Ser. No. 08/291,002, filed Aug. 15, 1994, now U.S. Pat. No. 5,549,924, which is a continuation-in-part of U.S. patent application Ser. No. 07/976,881, filed Nov. 16, 1992, now U.S. Pat. No. 5,338,565, which is a continuation of U.S. patent application Ser. No. 07/825,546 filed Jan. 24, 1992, now U.S. Pat. No. 5,165,953, which is a continuation-in-part of both U.S. patent application Ser. No. 07/536,772 filed Jun. 12, 1990, now U.S. Pat. No. 5,130,159 and U.S. patent application Ser. No. 07/536,773 filed Jun. 12, 1990, now U.S. Pat. No. 5,128,168, both of which are continuations-in-part of U.S. patent application Ser. No. 07/482,978 filed Feb. 22, 1990, now U.S. Pat. No. 5,045,341, which is a continuation-in-part of U.S. patent application Ser. No. 07/246,337 filed Sep. 19, 1988, now U.S. Pat. No. 4,935,260, which is a continuation-in-part of U.S. patent application Ser. No. 07/143,184, filed Jan. 13, 1988, now U.S. Pat. No. 4,919,966, which is a continuation-in-part of U.S. patent application Ser. No. 07/074,629, filed Jul. 17, 1987, now U.S. Pat. No. 4,771,482. All of these applications and patents are owned by the same Applicant. The entire disclosures of each of the foregoing patent applications and patents are hereby incorporated by reference herein.

BACKGROUND OF THE INVENTION

The present invention relates to membranes formed from materials including latex, polyurethane, polyethylene, rubber, and other polymers and elastomers. Known applications of such membranes include surgical and examination gloves, condoms, diaphragms, dressings, sheaths, slippers, overshoes, sterile bands, catheters, tubing, drapes, gut openings, mouth pieces, baby nipples, intra gastric nasal tubes, nasal gastric tubes, kidney shunts, eye and brain shunts, dental dams, dental braces, sub-clavian vein and artery shunts, and colostomy bags. Typically, such membranes in use contact a person's or animal's skin or other tissues.

In recent years, there has been a growing interest in improving such membranes to provide increased protection against the transmission of viruses such as hepatitis and HIV, as well as other pathogens and harmful agents.

SUMMARY OF THE INVENTION

The present invention discloses several embodiments which provide membranes with an improved resistance to transmission of viruses and other harmful agents, and capabilities to disinfect needles and other membrane piercing objects, and also discloses the provision of one or more indicating layers to detect and indicate membrane breach and the presence of viruses, and other pathogens, as well as harmful chemicals.

In one aspect of the invention, a membrane of multi-layer construction includes one or more inner-layers, which serve as reservoirs for substances or agents such as biocides, lubricants, or indicators, which can pass through one or more permeable or semi-permeable outer layers to make the reservoir substance available on the outside of the membrane, or to alternatively prevent exterior transmission of reservoir substances while allowing exterior substances to pass at least partially through the membrane. As an alternative to permeability, substantially impermeable layers may transmit the substance or agent upon rupture or piercing and completely contain the substances at all other times.

According to another aspect of the invention, a membrane of multi-layer construction includes one or more inner-layers, which serve as reservoirs for substances or agents such as biocides, lubricants, or indicators, which can contact or otherwise interface with substances passing through one or more outer layers of the membrane and which may react with, indicate the presence of, or otherwise respond to the presence of the substance originally outside the membrane. Such multi-layer membranes can be used to provide anti-microbial, disinfectant, or other killing or disabling action to infectious agents, microbes, viruses, or bacteria, through selective or controlled flow of the inner substances or agents to the surface of the membrane.

According to another aspect of the invention, a multi-layer membrane provides a site for indicating materials such as a DNA probe based reaction such as Chiron's "Branched DNA Probe", Hoffman-LaRoche's "Polymerase Chain Reaction" technique, or conventional color change indicator reactions, titration reactions, reactions to detect Ph, and reactions to detect chemicals, viruses or other pathogens. The-multi-layer membrane includes one or more permeable or semi-permeable layers to allow migration of a material to be detected through one or more outer layers and into contact with an indicating material or system. One or more of the layers may be impermeable to prevent migration beyond the indicators or other reservoir materials.

In another aspect of the invention, indicators to detect chemicals, viruses, or other pathogens are admixed with the material of the membrane, or with a layer of a multi-layer membrane, or coated on an outer layer of the membrane or multi-layer membrane.

Another aspect of the invention involves the provision of an indicator to indicate a breach of a membrane. Indication may be provided by color change, shade change, e.g., darker or lighter, temperature change, or tactile change, e.g., stiffness or tightness. Indicators such as cobalt chloride can indicate membrane breach by reacting in the presence of moisture.

In another aspect of the invention, a permeable or semi-permeable membrane of multi-layer construction includes one or more inner-layers which serve as reservoirs for substances or agents such as biocides, lubricants, hydrogels, or indicators. The substances or agents can pass through the outer layer or layers to make the reservoir substance available on the outside of the membrane.

In another aspect of the invention, one or more semi-permeable or permeable membrane layers permit migration of a substance in a predetermined direction. For example, viruses or other pathogens may migrate inwardly into contact with an indicator or biocide. Additionally or alternatively, biocides, lubricants, spermicides, antiseptics, or indicators, may migrate outwardly.

In another aspect of the invention, a single or multi-layer membrane includes an indicator located on an inner or outer surface to detect the presence of a virus or other harmful material disposed exteriorly of the membrane and/or also indicate transmission of a harmful material either partially or entirely through the membrane.

Another aspect of the invention includes the provision of a tactile-feeling enhancing liquid or gel between layers of a multi-layer membrane.

Another aspect of the invention involves the dispersion of micro-fibers or fibers such as Kevlar within or onto a membrane forming substance prior to or during membrane formation to increase membrane strength and penetration resistance.

In one aspect of the invention, the membrane includes an indicator which provides a prompt identifiable reaction in the presence of a harmful substance to alert a user. Example indicators include a DNA probe such as those developed by Chiron or Hoffman-LaRoche to detect the presence of particular viruses, or conventional color change indicator technology such as phenolphthalein reactions or Ph indicator materials, chromophores, or dyes which change in the presence of the substance to be detected.

In one aspect of the invention, a single or multi-layer membrane effects transport across one or more membrane layers by capillary or wicking action. The membrane or one or more layers may also constitute a size selective membrane to limit the size of viruses or microbes passing through. Additionally or alternatively, one or more of the membrane layers may be chemically selective. For example, membranes of the type used in filtration and purification procedures may be employed.

In another aspect of the invention, a membrane including a permeable or semi-permeable outer or inner layer includes a sealing treatment or coating to entrap indicators or biocide agents therein.

The invention also contemplates the provision of an indicator dispersed throughout a membrane or restricted to a certain spot or area on or in the membrane, such as in or on dots or stripes. The indicator may be added to the membrane during formation or after completion.

In another aspect of the invention, a needle treatment substance in one or more inner layers of a membrane functions to clean, coat, wipe, scrape, cleanse, disinfect, render less harmful, or otherwise treat a needle or other membrane piercing object.

Another aspect of the invention discloses a method of making a multi-layered membrane, such as a glove or condom, in which the layers are joined in one or more predetermined regions, such as only in a cuff or top region.

In another aspect of the invention, a method of admixing protein binding biocides such as gentian violet with wet latex prior to membrane formation increases membrane strength and/or reduces or eliminates allergic affects in latex-allergic or sensitive individuals.

In another aspect of the invention an adhesive backed patch includes an antiseptic or cleansing agent which contacts a needle or catheter piercing therethrough.

DESCRIPTION OF THE PREFERRED EMBODIMENTS

Needle Treating Layer

Needles, both hollow core and solid, as well as other sharp objects such as catheters, scalpels, wires, or bone fragments, have long been a concern for health care professionals and others in regard to the infection which they can transmit. Needles are usually in sterile condition when removed from their wrappers, however they can be inadvertently contaminated when they pass through a person's body and are potentially contaminated when they are removed from an infected patient's body.

It is common for health care workers and hospital staff to be accidentally stuck by needles or other sharp objects both during and after their use.

Pursuant to the present invention, a material is incorporated within a multi-layer membrane, such as a glove, to clean, coat, wipe, scrape, cleanse, disinfect, render less harmful or otherwise treat a needle or other sharp object passing therethrough.

A membrane formed from liquid latex, solvent cast membranes, liquid polymers or other synthetics, or elastomers may be formed by dip forming, the use of fluidized beds, or spraying the liquid material onto a former. After deposit of one or more layers, a middle layer including a material having treatment properties is deposited. Thereafter, one or more outer layers are formed and the membrane is cured or set according to conventional techniques.

Suitable polymers for use in producing membranes pursuant to the invention include prepolymers, i.e. low molecular weight polymers and polymer precursors, prepolymers and polymer precursors dissolved in solvents, liquid monomers, and liquid monomers dissolved in solvents. Specific examples include low molecular weight polymers such as silicone rubber (polydimethyl siloxane: $HO-(Si-(CH_3)_2-O-)_n-H$) with n from 2 to 200; polymer precursors such as low molecular weigh diol, e.g. $HO-((CH_2)_4-O)_{18})-H$ and low molecular weight diisocyanate, e.g. $OCN-C_6H_6-CH_2-C_6H_6-NCO$ which when mixed and polymerized form polyurethane. Example solvents for low molecular weight polymers include xylene and n-hexane. Suitable solvents for polymer precursors include dimethyl formamide and dimethyl sulfoxide. Example liquid monomers include alpha-alkyl cyanoacrylate, where the alkyl group can be -methyl, -ethyl, -propyl, etc. Example solvents for liquid monomers include dimethyl formamide. In the context of this description, the terms prepolymer, polymer, and polymer precursors include mixtures of one or more prepolymers, polymers, or polymer precursors.

In one embodiment of the invention, the needle or sharp object treating layer comprises a gummy coating such as urethane of a gum-like consistency, semi-cured latex, a gel, polymers, an adhesive, or a pituitous substance, with or without an admixed biocide, antiseptic, or sterilizing agent, as an inner layer.

As the needle or other object pierces the membrane, the treatment substance tends to stick to it, coat it, cleanse it, or otherwise deactivate any harmful substances which might adhere thereto. The mechanics of the needle or sharp object treatment mechanism may include both chemical and mechanical aspects. For example, the layer preferably includes a biocide or antiseptic effective against pathogens. Additionally, the layer may also function to wipe blood and other bodily fluids from the needle as it passes therethrough.

Alternately, abrasive materials of a fine texture capable of physically dislodging or scraping materials coated on the needle may be used individually or in combination.

Example treatment chemicals added to a biocide in the inner needle treatment layer include polyethylene oxide, and a mixture of polyethylene oxide and glycerin. In forming latex membranes, a first latex layer is deposited by dipping or spraying or by other conventional techniques. A biocide, such as a gentian violet solution, is thickened with a mixture of polyethylene oxide and glycerin. The thickened mixture is applied over the latex layer, allowed to dry to some extent, and then coated with one or more latex layers.

The needle treatment layer may also include adhesive or film-forming materials which would form a physical sheath or additional membrane over the needle or other sharp object and over other harmful agents thereon.

The needle treating layer or layers may also include a detergent or other agent which will modify the surface tension properties of harmful agents on the needle rendering it possible for a subsequent layer to physically remove, contain, disinfect, or render less harmful the harmful agent, or for it to be less prone to infect or contaminate the person or animal on the opposite side of the membrane.

The aforementioned approaches may be used individually or in combination and may be contained in the same layer or in separate layers of a multi-layer membrane. They may be coagulants or not and the use of natural latex and man-made latex or polymers or elastomer substitutes may be interchangeable.

Needle Treatment Patch

A needle treatment patch and a method for its use in assisting in disinfecting a needle or other sharp object after or during its use are described below.

In one embodiment a small adhesive backed patch or disc can be attached to the area which the needle is set to penetrate. The disc can be similar to a squashed or flattened vitamin E pellet which the needle pierces before piercing the skin. The disc includes an antimicrobial, antiseptic or cleansing ingredient which contacts the needle prior to piercing the skin and upon exiting the skin. The disc may be transparent to assist a health care professional in locating a vein or other target. Likewise, the adhesive may be disposed only around the outer periphery of the disc so that it would not be carried into the puncture.

The back side of the patch may include a biocide or antiseptic adapted to contact the skin of a patient or animal.

The disc may be constructed such that the weave or pattern allows penetration by the needle or syringe upon entering and then creates a wiping action upon being withdrawn back through the disc. The patch preferably includes an antimicrobial or disinfecting solution.

The biocide or antiseptic solution contained in both embodiments may be of a gel-like and/or sticky consistency to help coat the needle or seal it on the way out of the body or patch.

The patch may also be used in conjunction with insertion or attachment of catheters and ostomy products, and may be employed in conjunction with long term attachment of a catheter to inhibit growth and/or transmission of pathogens.

Suitable patch adhesives, as set forth in U.S. Pat. No. 5,2345,957, the entire disclosure of which is incorporated by reference herein, include partially esterified polyacrylic acid polymers, including but not limited to, polyacrylic acid polymers crosslinked with a polyalkenyl polyether such as those commercially available from B. F. Goodrich, Cincinnati, Ohio, under the trademarks Carbopol 934, 934P, 940 and 941. Other suitable adhesives include natural or synthetic polysaccharides such as cellulose derivatives such as methylcellulose, cellulose acetate, carboxymethylcellulose, hydroxyethylcellulose and the like. Other suitable adhesives are pectin, a mixture of sulfated sucrose and aluminum hydroxide, hydrophilic polysaccharide gums such as natural plant exudates, including karaya gum, ghatti gum, tragacanth gum, xanthan gum, jaraya gum and the like, as well as seed gums such as guar gum, locust bean gum, psillium seed gum and the like.

Suitable biocides for use in membranes according to the disclosure of the instant application include phenols, acridine dyes, gentian violet (crystal violet), chlorhexadine, Triclosan, Nonoxynol 9, Gluconate, dextran sulphate, benzalkonium, betadyne, mercurochrome, silver salts, and an extract of blue-green algae, in addition to a long list of other suitable biocides appended to this description immediately prior to the claims.

Indicators And Multi-Layer Membranes

In most surgical settings the physician or surgeon does not know if the patient has a communicable disease carried by blood borne pathogens. It would be beneficial, especially for those in the operating room and emergency room, to have an indicator on their glove that would alert them when they are in contact with the patient's blood or body fluid that there is the presence of a harmful, contagious or potentially fatal substance in that fluid or blood.

The present invention contemplates the provision of indicating mechanisms to multi-dipped or solvent formed membranes, including, but not limited to, gloves and condoms. The present invention discloses the provision of indicators to alert a user to membrane breach, as well as to alert a user of dangerous substances present in blood and other body fluids.

As disclosed in U.S. Pat. No. 4,935,260, fluid reservoirs within a membrane may include colored, fluorescent, or reactive substances which serve as an indicator if the membrane is breached, defective or disturbed. The present invention contemplates the provision of a visual indication to a user of membrane breach by color change or appearance or other physical means.

An indicating change to a material in an inner layer of a multi-layer membrane can be triggered by the presence of air, moisture, body fluids, harmful substances, change in electrical activity, surface tension, or partial pressure. The indicating system responds to an exposure of the indicating element to an outside substance or change in the physical integrity of the surrounding membrane. Ph change in the inner material because of exposure to substances outside the membrane can be an additional indicating mechanism.

Other suitable indicators for use in membranes according to the present invention include indicating materials such as a DNA probe based reaction such as Chiron's "Branched DNA Probe", Hoffman-LaRoche's "Polymerase Chain Reaction" technique, or conventional color change indicator reactions, to detect chemicals, viruses or other pathogens. A multi-layer membrane may include one or more permeable or semi-permeable layers to allow migration of a material to be detected through the outer layers and into contact with an indicating material or system. Other suitable viral indicators and indicating methods are disclosed in U.S. Pat. Nos. 4,879,211; 4,942,122; 5,039,604; 5,093,230; 5,108,891; 5,149,623; 5,156,949; 5,208,321; 5,235,039; 5,260,189; 5,268,265; the entire disclosure of each of which are hereby incorporated by reference herein.

A method of making a membrane including a color indicator for membrane breach is set forth below.

1. Using conventional dipping, spraying, or other sheet forming techniques an initial layer is formed using elastomer materials such as latex, solvent cast membranes, liquid polymers, or elastomers, or polymer films. A second layer is created by conventional techniques such as coating or dipping (with or without a coagulant) including an indicating material such as dyes, crystals, reactants, colored agents, or congealing substances.

2. The dyes or indicators are selected to provide a noticeable change in appearance, feel, (stiffness, clumpyness, consistency), or temperature, to indicate to the user that the membrane is compromised.

3. One or more additional elastomeric membrane layers are then formed to at least partially contain the indicating substance.

The present invention also contemplates the provision to a multi-layer membrane of an indicator to detect and indicate the presence of pathogens in blood or other bodily fluids.

Outer membrane layers selected to be either impermeable, permeable, or selectively permeable to a substance included in a reservoir created between membrane layers, or to the substances, microbes or pathogens whose presence is to be detected. Instead of, or in addition to, the inclusion of various substances in a reservoir formed between membrane layers, the substances may be applied to inner or outer surfaces of the membrane after formation.

Multi-layer gloves according to the present invention, in addition to or instead of indicators, may also include one or more reservoirs disposed between adjacent membrane layers and containing one or more substances such as lubricants, biocides, spermicides, antiseptics, gels, hydrogels, pituitous substances, cleansing agents, surfactants, detergents, abrasives, coating agents, wiping agents, fibers, tactile enhancing objects, and sheet forming agents, such that said substance is substantially contained between the adjacent layers. One or more of the multiple membrane layers may be permeable or semi-permeable to allow directional migration of (1) reservoir substances exteriorly to the membrane, or (2) exterior substances at least partially through the membrane.

Figure 4:
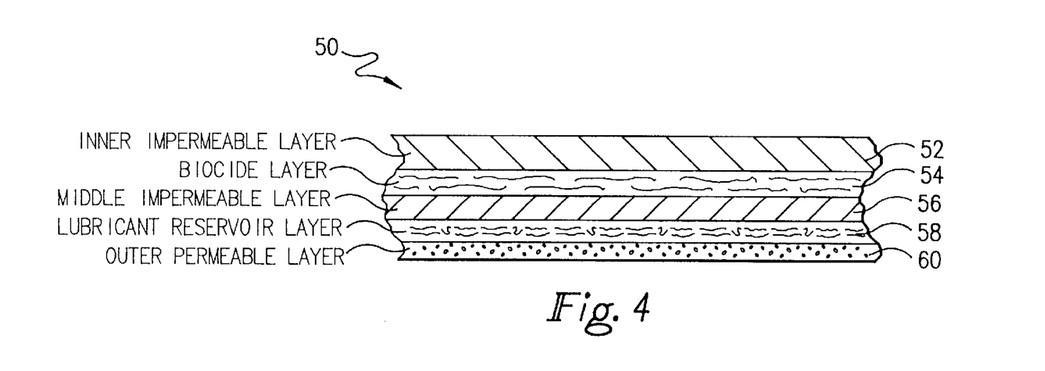
FIG. 4 is a cross-sectional view illustrating an example multi-layer membrane according to the present invention.

An example multi-layer membrane 50 according to the present invention is illustrated in FIG. 4. The membrane 50 may, for example, comprise a condom. An inner impermeable layer 52 may be formed from latex or from a polymer material. A biocide and/or spermicide such as Nonoxynol 9 at least partially fills a reservoir 54 formed between the inner layer 52 and a middle or intermediate impermeable layer 56, which may also comprise a latex or polymer material. A lubricant fills a reservoir 58 formed between the intermediate layer 56 and an outer permeable layer 60 to effect a controlled release of the lubricant through the pores of the permeable layer 60 over time. The permeable layer 60 may comprise a membrane with pores which open to permit the lubricant from reservoir 58 to pass through when stretched under pressure.

In the event of breach of the inner layer 52, seminal fluids will initially contact the biocide/spermicide in the reservoir 54, even in the event of a concurrent breach of the intermediate layer 56. Similarly, in the event of breach of the intermediate layer 56, vaginal fluids will also initially contact the biocide/spermicide in the reservoir 54, even in the event of a concurrent breach of the inner layer 52.

The methods of introducing or forming the inner layer or one or more intermediate or outer layers of multi-layer membranes pursuant to the present invention include dip forming methods and other techniques such as spray coating, sheet forming techniques, fluidized bed deposition, vapor deposition, electrical discharge deposition, vacuum deposition, centrifugal coating, and extrusion. Molding techniques, such as rotational molding, or other types of molding techniques employing positive or negative mold surfaces may be employed.

Membranes or membrane layers pursuant to the invention may also include latex, elastomer, or polymer or synthetic films where the membrane or membrane layer is coated with a desired substance such as biocides, lubricants, indicators, spermicides, antiseptics, gels, hydrogels, pituitous substances, cleansing agents, surfactants, detergents, abrasives, coating agents, wiping agents, fibers, tactile enhancing objects, and sheet forming agents, and is then surface treated to contain the coated substance. Examples of such surface treatment methods include treatment with a chemical such as chlorine or bromine, coating with a sealant such as silicone or an acrylic, a heat treating process such as melting or glazing, treatment by exposure to reduced temperatures, mechanical treatment processes such as rolling, pressing, ultrasonics, or radio frequency heating. In each instance the common objective is the substantial containment of a desired substance on a surface of an inner, intermediate, or outer membrane layer.

The surface on one side may be designed to be impervious while the substance on the other side of the multi-layer membrane may be designed to be permeable or selectively permeable.

The indicator may be provided on an interior surface of single or multi-layer membranes, or on the outer surface, where it can be exposed to a pathogen or harmful substance or antibody of a harmful substance.

Figure 3:
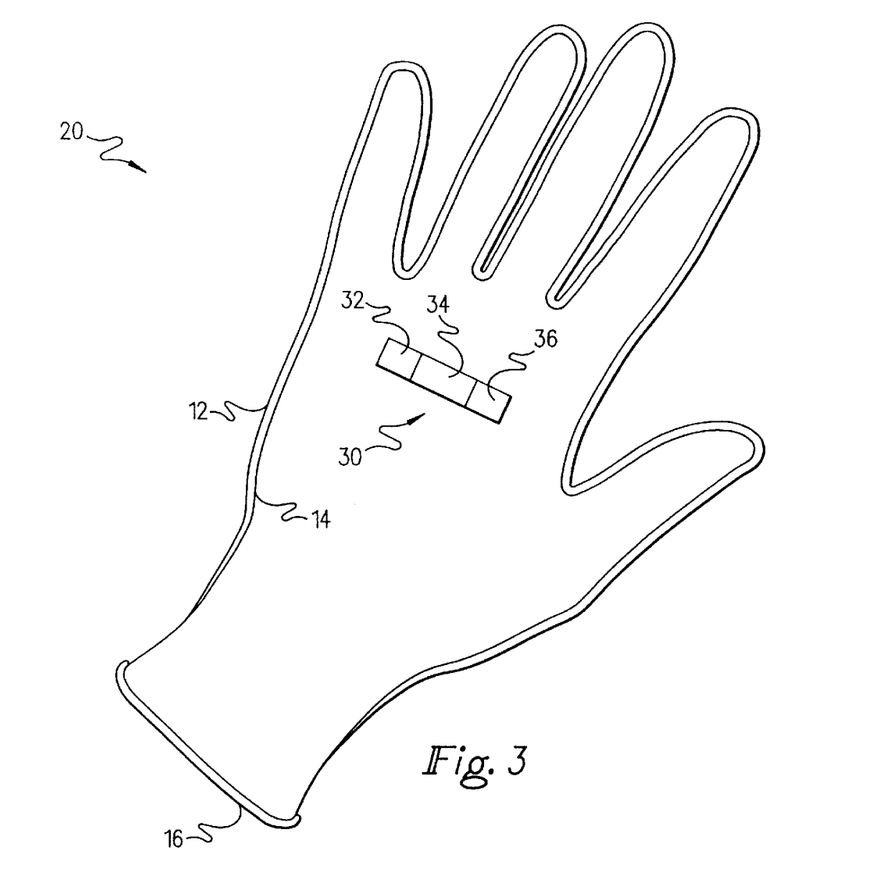
FIG. 3 is a diagrammatic plan view illustrating a double glove according to the present invention having an indicating strip with separate detecting regions to indicate the presence of different pathogens or other harmful agents or chemicals in the environment of the glove user.

FIG. 3 illustrates an example glove 20 according to the present invention which includes inner 14 and outer 12 layers joined at a cuff region 16. An indicating strip 30 bonded or otherwise attached to the outer surface of the glove 30 includes separate indicators in boxes or regions 32, 34, and 36 for detecting and indicating to the user the presence of pathogens or other harmful agents or chemicals in the user's environment. For example the indicator bar may show the presence of Strep in box 32, the presence of a retro-virus in box 34, and the presence of Staph in box 36.

The indicating substance may be more effectively retained by the membrane if the membrane comprises a film selected from the family of glow discharge treated polymers, such as polyethylene, tetrafluoroethylene PE (TFE/PE), polyethyleneterephthalate (PET), TFE/PET, polytetrafluoroethylene (PTFE), ehtylene glow discharge treated PET (E/PET) and hexamethyldisiloxane glow discharge treated PET (HMDS/PET).

The indicator preferably included in multi-layer membranes produces an identifiable reaction, alerting the wearer to the presence of a potentially harmful substance.

Indicators may be specific for any number of substances and microorganisms, including viruses (including HIV), bacteria, yeasts, undesirable and harmful chemicals, etc Specific viral indicators may include DNA Probe based reactions such as Chiron's "Branched DNA Probe", Hoffman-LaRoche's "Polymerase Chain Reaction" technique, the elements of the P-24 antigen kit, the Abbot Lab preparation or mixed preparation for GP-120.

Additional examples of indicators include conventional color change indicator reactions where the material to be detected (pathogen, chemical, or other substance) could migrate through the outer membrane and reach the indicator system. Similarly, certain of these indicators could be admixed with the material of the membrane or a layer of the multi-layer membrane or coated on the outer layer of the membrane or multi-layer membrane.

For example, HIV and Hepatitis B belong to a family called the retro-virus family. Indicators that could pick up the presence of HIV or its antigens in blood are the P-24 antigen kit, and the Abbot Lab preparation or mixed preparation for GP-120. In addition, other tests can pick up indications of the presence of a retro-virus or a lenti virus by reacting with a substance common to the virus family, like the envelope of the virus family. Indicators may also pick up anti-bodies to these harmful substances in bodily fluids such as blood, semen, or vaginal fluid. And it is particularly noted that one specific substance may be picked up instead of a family of harmful substances. Some of these indicators may be, but are not necessarily limited to, the family or group of synthetic peptides and epitopes.

Transdermal Trigger

When a glove is in use, a defect can sometimes be detected by various leak detector devices—some utilizing changes in the electrical properties or patterns of the material or material surface. These are of little benefit if the wearer is not in a position to change his gloves and remove the defective glove or pull another glove over it.

The present invention discloses a glove constructed in a multi-layered manner that contains a chemical that may be triggered to be released inside the glove, next to the hand to protect the wearer, until the time when he or she can take proper action.

The technology applied to the membrane is similar to existing transdermal patch technology. This technology is in use in nicotine patches and hormone releasing patches. They can provide a sustained release or a specific release upon a change in the electrical properties on the surface of, or a breach in integrity of, the membrane. Examples of transdermal patches are disclosed in U.S. Pat. Nos. 4,286,592; 4,627,429; 4,839,174; 4,921,475; 4,978,531; 5,008,110; 5,087,240; 5,163,899; 5,164,189; 5,230,896; 5,234,957; 5,262,165; 5,273,756; and 5,286,490; 5,290,561; the entire disclosures of each of which are hereby incorporated by reference herein.

The multi-layer glove preferably contains a reservoir of antiseptic/disinfectant which is released through the transdermal system upon deterioration of the glove film as indicated by a change in electrical properties, the presence of moisture or other indications of decrease in glove integrity.

Double Layer Membrane Dip Forming Method

In many applications, use of a double layer membrane can provide increased protection. For example, it is now an accepted practice for surgeons and other health care practitioners to don two pairs of gloves, one over the other to provide maximum protection from infection. Indeed, some studies show that the use of two gloves worn together reduces the occurrence of infection.

Such a double layer membrane configuration also creates a space which can serve as a reservoir, particularly when the layers of the membrane are joined at a cuff or top region. This reservoir can be used to contain a variety of materials including biocides, needle treating materials, tactile enhancing liquids or gels, lubricants, spermicides, hydrogels, indicators, and scales, discs, or other materials for inhibiting penetration of needles and other sharps.

Hydrogels may be of the type disclosed in U.S. Pat. No. 4,499,154, the entire disclosure of which is incorporated herein by reference. Hydrogels may function to absorb a biocide and to hold membrane layers apart, and can function as a coagulant or as a lubricant.

Examples of lubricants within the scope of this application include water soluble nontoxic chemical compounds that incorporate sodium or potassium in varying chemical combinations with carbonates, acetates, bicarbonates, acetate trihydrates and citrate dihydrate, as disclosed in U.S. Pat. No. 4,143,423, the entire disclosure of which is hereby incorporated by reference herein. Other suitable lubricants include microspheres as described in U.S. Pat. No. 5,073,365, the entire disclosure of which is hereby incorporated by reference herein.

It is possible to form a double glove or other double membrane in a multi-dip manufacturing process. Latex gloves and condoms are conventionally produced using a dip forming method in which shaped formers are dipped into vats of liquid latex. A method of making a double layer latex membrane pursuant to the present invention includes the following steps:

1. Clean formers.
2. Heat formers for eight minutes at 210–220 F. degrees.
3. Dip into coagulating solution such as $CaCO_3$ plus alcohol plus $NO_3$, (or Calcium Carbonate plus alcohol plus nitrate).
4. Stand 2–3 minutes.
5. Dip into uncured latex.
6. Stand 2–3 minutes.
7. Leach with cold tap water for 15 minutes . . . stand 2 minutes.
8. Produce ring roll.
9. Dry in oven 6 minutes.
10. Dip into 1.5% solution gentian violet in distilled water. (May substitute other biocides or chemicals in various solutions, or optionally eliminate biocide dip, as it is possible to make a double glove or other membrane without use of a biocide).
11. Dry in oven.
12. Stand 5 minutes.
13. Dip in 20% or greater concentration calcium nitrate coagulant.
14. Dip into uncured latex.
15. Stand 8 minutes.
16. Dry in oven for 30 minutes to cure by heating the membrane to dry them to their final form. p1 17. Powder and strip the doublet membrane from the former.

Figure 1:
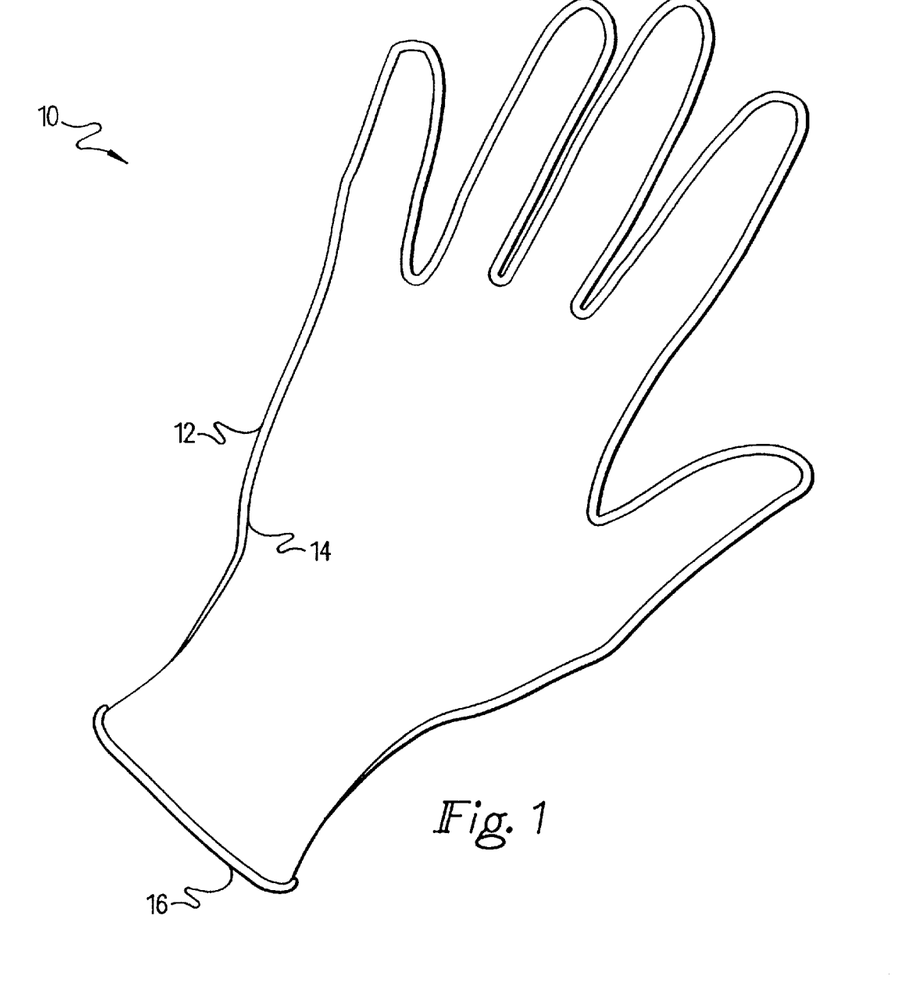
FIG. 1 depicts a diagrammatic plan view illustrating a double glove produced according to a method of the present invention.
Figure 2:
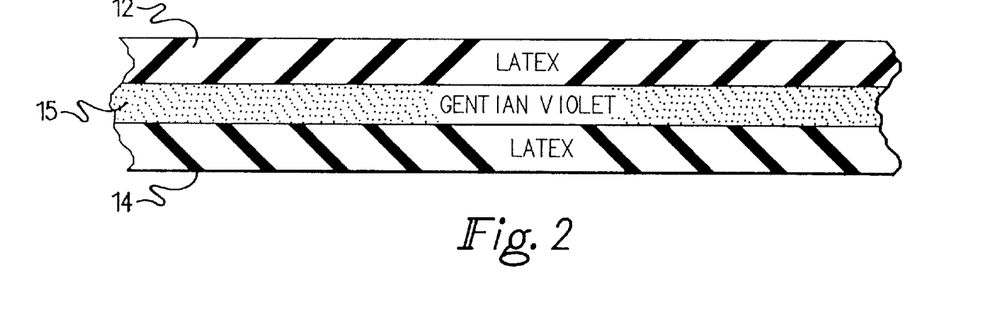
FIG. 2 is a cross-sectional view illustrating the double glove of FIG. 1 including a biocide disposed in an intermediate reservoir formed between inner and outer layers of the glove.

This method produces a glove within a glove or a condom within a condom joined at the cuff or top. FIG. 1 illustrates an example double glove 10 produced according to the invention which includes a discrete separated outer layer 12 and an inner layer 14 joined in the cuff region at a ring roll 16. As can be readily appreciated, the inventive double glove 10 has substantial advantages in ease of donning compared to separate single layer gloves. The space between the two membranes can be constructed with an additional step or steps of incorporating different substances including but not limited to gels, biocides, chemicals, silicones, neutralizing chemicals, buffering chemicals, spermicides, lubricants, tactile enhancers, and scales, discs, or other materials for inhibiting penetration of needles and other sharps. For example, as shown in FIG. 2, the reservoir 15 formed between the inner 14 and outer 12 layers of the glove may be filled with a biocide such as gentian violet.

It should be appreciated that this double membrane configuration can also be made by the above method with a biocide component by dipping in biocide before dipping in the coagulant, or by mixing the biocide or chemical with the coagulant.

The salient steps in the above method comprise:

(a) depositing onto a former a first latex layer;

(b) treating the first layer with a material effective as a coagulant for latex;

(c) depositing over the first layer on the former a second latex layer, with the coagulant effective to substantially prevent fusing of the first and second layers; and (d) setting or curing the first and second layers.

It is particularly preferred that the coagulant is not applied to a circumferentially extending top or cuff region of the first layer such that the first and second layers will fuse in the cuff region to form a reservoir in the remaining regions. Prior to application of coagulant to the first layer, a substance may be deposited over the first layer on the former, with the substance selected from the group consisting of biocides, indicators, spermicides, antiseptics, gels, hydrogels, pituitous substances, cleansing agents, surfactants, detergents, abrasives, discs, scales, and other materials for inhibiting penetration of needles and other sharps, coating agents, wiping agents, fibers, tactile enhancing objects, and sheet forming agents, such that the substance is substantially contained between the first latex layer and the second latex layer. Such intermediate substances may also be admixes for application with the coagulant.

In another example method of making a double latex membrane according to the present invention, such as "double gloves," a glove mold or former warmed to about 70 degrees C. is first dipped in a coagulant slurry in a conventional manner. This coating is dried in the oven at about 80 degrees C. for five minutes. The mold in then dipped in a latex compound, available under the designation Vultex 1-N-4402 at 38% solids from General Latex and Chemical corporation, with a dwell time of about five seconds. The deposit is then partially dried at 80 degrees C. for about one minute. The latex deposit is then leached in warm water for about three minutes and dried in the oven at 100 degrees C. for five minutes or until the latex deposit is completely dry.

A separating agent coating of zinc stearate water emulsion at about 3–5% solids is applied over the first latex layer on the former, except in a region within one to two inches of the cuff or bead area, by spraying or alternatively by dipping. The zinc stearate coating is then dried at about 100 degrees C. for about three to five minutes and a powder free coagulant is applied over the first latex coating. This coagulant coating is then dried at about 80 degrees C. for five minutes and then the former is again dipped into the latex compound, adjusting the dipping speeds to provide a uniform second layer. The second layer is then partially dried for about one minute at about 80 degrees C. and leached in warm water for about three minutes. The second latex layer is then cured at 125 degrees C. for twenty minutes. A coating of corn starch powder is applied, and the glove is then stripped from the former.

The resulting glove has two discrete layers, except in the one to two inch region of the cuff or bead, where the glove consists of a single layer.

The separating agent may be either applied after the second coagulant coating, or alternatively incorporated into the second coagulant formulation for concurrent application therewith.

A variety of different potential separating agent may be employed, including: zinc stearates and other stearates, hydrogel compositions, powders such as calcium carbonates, cornstarch, microspheres, wax emulsions such as parafin and micro-crystalline, silicon emulsions, gentian violet at high concentrations, silicon oils, acrylic separating compositions, separate curing of latex layers, and chlorination of the first latex layer before application of the second layers.

The formation of the second layer requires flexibility in regard to dipping speeds depending upon the particular formulations of latex, separating agent, and coagulants employed. For example, different dipping speeds may be employed in the cuff region (not coated with the separating agent) and the main body region, and/or the second layer may be double dipped in the main region and single dipped in the cuff region. Temperatures, speeds, and dwell times may also vary dependent upon the particular formulations employed.

A method of forming a polymeric multi-layer membrane according to the present invention includes the steps of:

(a) depositing onto a former a material selected from the group consisting of liquid polymers and polymers dissolved in a solvent to form a first layer;

(b) treating the first layer with a surfactant;

(c) depositing over the first layer on the former a material selected from the group consisting of liquid polymers and polymers dissolved in a solvent to form a second layer, wherein the surfactant is effective to substantially prevent fusing of the first and second layers; and (d) setting or curing the first and second layers.

As in the method of making latex membranes, a variety of substances may be provided in an. intermediate layer or reservoir between the first and second layers. Example surfactants include ionic surfactants capable of emulsifying or destabilizing polymers in a known manner. In the context of this application, the term polymer includes water based synthetic materials.

It is also believed possible to use other techniques to produce membranes having multiple discrete latex or polymer layers. For example, temperatures of the mold/former and/or the latex or polymer bath, leach bath, oven, and/or a surrounding chamber might be varied at different stages in the process. For example, the first latex or polymer layer might be cooled prior to application of the second layer to form separate layers in the resulting membrane. Additionally, application of sonic, ultrasonic, or thermal shocks might be employed to separate or facilitate separation of layers. Irradiation with energy of various frequencies of the electromagnetic spectrum might also be employed.

In the case of both latex and polymer or synthetic membranes, the first and second layers may be selectively fused or separated by selective application and/or variations in the formulation of the separating agent, coagulant or surfactant. For example the first and second layers might be fused or joined in selected areas of a glove such as the palm, the back of the hand, the knuckles, finger tips. Similar selective joining might be employed with other multiple layer membranes such as condoms. For example, multiple layers of a condom might be selectively in the tip and/or intermediate region. A bubble or blister effect may also be created by fusing two layers of a multiple layer membrane in such a manner to create discrete sealed chambers. Such chambers might contain a variety of different solids, liquids, and gasses such as lubricants, sealants, biocides, indicators, spermicides, antiseptics, gels, hydrogels, pituitous substances, cleansing agents, surfactants, detergents, abrasives, coating agents, wiping agents, fibers, tactile enhancing objects, and discs, scales and other materials for inhibiting penetration of needles and other sharps. For example, the chambers might contain liquids or gasses to provide a cushioning effect. Alternatively, the chambers might contain materials which combine upon rupture of the chambers to provide an indicating effect. Diverse materials might also be selected which combine to provide a color change, heating effect, disinfectant or biocide, stiffening, softening, or alteration in tactile sense.

It is also possible to vary the extent of separation or fusing of the layers of a multiple layer membrane by varying the chemistry of the latex or polymer, the chemistry of the separating agent, surfactant or coagulant, the cure times and temperatures, the dip speed and dwell times, and through other methods, such as chlorination. The extent of separation or fusing of the layers can range from completely discrete layers to layers which, although initially stuck together, may be peeled apart with some effort.

As an alternative to dip or spray forming of latex, synthetic, or polymer membranes having multiple discrete layers, the techniques described above may also be employed in connection with conventional sheet forming and extrusion processes to make a variety of other multiple layer membranes. For example, a multiple layer medical or other type of tubing may be formed using an extrusion process. As in the case of dip or spray forming techniques, the various layers of multiple layer membranes formed by sheeting or extrusion techniques may be joined or fused in selected regions and separated or discrete in other selected regions. Such multiple layer membranes find applications in applicances where an added measure of security against rupture is desired, for example in colostomy bags.

The grain or other characteristics of the individual latex or polymer layers of a multiple layer membrane might be different. For example, the former might be differently inclined and/or rotated in forming different layers to provide an enhanced strength membrane. Alternatively, different layers might be applied during application of different electrostatic or magnetic fields. Further, the various layers might be formed of different materials such as latex, polymers, and synthetics, possibly treated in various different manners, such as by conventional chlorination treatments of latex layers.

Incorporation Of Biocide Into Polyurethane Films

Glow discharge treatment techniques can be used to enhance the pick-up and retention properties of certain polymer families.

Biocides may be more effectively picked up and retained by certain polymer films. The film may be selected from the family of glow discharge treated polymers, such as polyethylene, tetrafluoroethylene glow discharge treated PE(TFE/PE), polyethyleneterephthalate) (PET), TFE/PET, polytetrafluoroethylene (PTFE), ethylene glow discharge treated PET (E/PET) and hexamethyldisiloxane glow discharge treated PET (HMDS/PET), or any of the other polymers treated by the glow discharge process. The biocides may be directly applied to the glow discharge treated films. The resulting films may be somewhat stiffer but very strong and therefore thinner films will be satisfactory for many applications.

Alternately, the biocides may be fed, as a gas, into a chamber and directly deposited by creating the glow discharge or RF discharge to facilitate the deposition.

Additionally, the biocides may be introduced on, and/or into the polymer during the fabrication of the film in such a way as to be available to provide disinfectant properties. This can be accomplished by conventional dipping or mixing, with additional layers deposited by dipping, casting, spray coating, vacuum depositing, passing through fluidized beds, centrifugal spinning, etc. Outer coats can be formed by similar techniques to contain the biocide and minimize leaching where desirable.

Coatings within the scope of the present invention include spermicides such as Nonoxinol-9 and one or more organopolysiloxane compounds which may be applied to latex membranes as disclosed in U.S. Pat. No. 5,304,375, the entire disclosure of which is hereby incorporated by reference herein. Rubber membranes may be provided with a transparent coating of an aqueous composition containing a preformed latex binder, an emulsifying agent, an inorganic fluoro-containing compound, and a thickening agent as described in U.S. Pat. No. 5,182,142, the entire disclosure of which is hereby incorporated by reference herein. A cellulosic coating material including synthetic latex formed by emulsification of cellulosic polymers stabilized by surfactants and containing a water-soluble pore forming agent and a plasticizer may also be employed, as described in U.S. Pat. No. 5,126,146, the entire disclosure of which is hereby incorporated by reference herein.

Incorporation of Biocide Into Porous And Non-Porous Polyurethane Films

This can be done in the four ways described below. All except the last require the biocide to have a low vapor pressure at room temperature (less than −0.013 bar). In all cases the solvents that come in contact with the biocide must not react with or chemically alter the biocide in such a way as to irreversibly destroy their anti-bacterial and anti-viral activity.

(1) Physical entrapment of the biocide in the pores of a porous film.

A. Introduction of the Biocide During Fabrication of the Film

Such films can be fabricated using (1) a fully polymerized polyurethane dissolved in a suitable solvent, or (2) using a polyurethane prepolymer of molecular weight 1000 to 3000 dissolved in a solvent and subsequently vulcanized or cured with a crosslinking or curing agent added to the solution. In both cases, the solvents must be solvents for both the biocide and the polyurethane.

The solvents for this purpose will depend on the type of polyurethane: polyether, polyester or polyester-polyamide, and on the type of biocide. Some candidates are listed in the table below.

Table I. Candidate Solvents and their Solubility Parameters.

| Solvent | Solubility Parameter $(cals/cc)^{1/2}$ | Hydrogen Bonding |
|---|---|---|
| Dimethyl formamide (DMF) | 12.1 | medium |
| Dimethyl acetamide (DMF) | 10.8 | medium |
| Tetrahydrofuran (THF) | 9.1 | medium |
| Dimethyl sulfoxide (DMS) | 12 | medium |
| Dioxane 1,4 | 10 | medium |
| Phenol | | strong |
| m-Cresol | 10.2 | strong |
| Formic acid | 12.1 | strong |
| Sulfuric acid | | strong |
| Methyl ethyl ketone | 9.3 | medium |
| Diethyl ketone | 8.8 | medium |
| Ethylene glycol monoethyl ether | 10.5 | medium |
| Ethylene glycol monomethyl ether | 11.4 | medium |

The use of water soluble polymers is also contemplated within the scope of the instant invention.

Mixtures of these solvents with each other and with non-solvents having solubility parameters in the range: 8 to 24 $(cals/cc)^{1/2}$ and medium or strong hydrogen bonding are also candidates.

The biocide is first dissolved in such a solvent or solvent mixture, to form a nearly saturated solution, and is then mixed with a solution of the polyurethane or urethane prepolymer in the same or similar solvent. In the case of solutions containing the polyurethane prepolymer, the curing agent (typically amines or alcohols with functionality of 2 or more) is added to the polymer plus biocide solution just prior to casting the films. Films of the resulting mixture are then cast using the methods described in the Gilding patents: U.S. Pat. Nos. 4,813,966 and 4,704,130, the entire disclosures of which are hereby incorporated by reference herein, with the following modifications.

On immersion of the cast film in the precipitation bath, and subsequently in the solvent extraction bath, there will be a tendency for the biocide to be leached out of the rubber and into the bath solution. This leaching can be reduced in two ways (1) saturate the precipitation or extraction bath with the biocide, or (2) use liquids of low polarity (having solubility parameters less than −9 $(cals/cc)^{1/2}$ and weak hydrogen bonding) in the precipitation and extraction baths. Since most biocides are strongly polar, they will tend to remain in the medium to strongly polar environment of the polyurethane rather than be extracted into the bath.

On subsequent drying and annealing, the remaining solvent is removed leaving the biocide physically trapped in the pores of the film.

B. Introduction of the Biocide Subsequent to the Fabrication of the Film

A porous polyurethane film can be swelled with a solvent or solvent mixture from Table I, or with a mixture of such solvents with non-solvents, saturated with a biocide. In the case of a linear polyurethane, the proportion of non-solvent must be adjusted so that the solvent mixture swells the soft segments (polyether segments) of the urethane chain, but does not dissolve the polymer. During the swelling, the solvent/swelling agent carries the biocide through the polymer structure and into the pores.

After removal of the film from the biocide solution, the film is dried and annealed, which removes the swelling agent and leaves the biocide trapped in the pores as well as in the polymer matrix.

(2) Adsorption of the Biocide on Internal Pore Surfaces

This method is applicable to porous films.

The same procedures as in 1A and 1B are followed except that the extraction of the solvent or swelling agent from the rubber is accomplished mostly by immersion of the film in a non-solvent bath of low polarity (solubility parameter less than 9 $(cal/cc)^{1/2}$ and weak hydrogen bonding). In this case, the non-solvent bath is not saturated with the biocide, as a consequence there will be a strong tendency for the biocide to adsorb to the polar polyurethane pore surfaces (as well as being trapped within the rubber matrix). The non-adsorbed biocide molecules in the pores will be leached out into the non-solvent leaving the adsorbed biocide on the pore surfaces. Any solvent or on solvent remaining in the films can be removed by drying and annealing.

(3) Precipitation of the Biocide within the Rubber Matrix

This method is applicable to non-porous urethane films.

The same procedures as in 1A and 1B are used except that the methods for producing the pores, described in the Gilding patents are not applied. Instead, the films are simply cast from solution using the common film forming procedures: dip-coating, spraying, spinning, etc. In the case of prefabricated films the diffusion of the swelling agent plus biocide can be enhanced by stretching the rubber film biaxially.

Extraction of the solvent/swelling agent is accomplished by drying and annealing. A non-solvent bath saturated with biocide can also be used as in (1) but drying is preferred. As the concentration of the solvent/swelling agent in the rubber decreases, the biocide will precipitate out forming phase-separated regions within the rubber matrix.

(4) Chemical Bonding of the Biocide to Functional Groups on the Polyurethane Chains. This method is applicable to both porous and nonporous films Polyurethanes possess the advantage that the urethane and urea linkages in the chains are relatively reactive. Furthermore, the rubber can easily be formulated to have excess amine, —OH or isocyanate groups at chain ends or branch points, simply by deviating slightly from the stoichiometric proportions of 1:1 isocyanate: amine groups or isocyanate: —OH groups.

The biocide molecules can then be chemically bonded to such groups. It is important that such bonding be accomplished in such a way that the biocidal activity of these molecules is not compromised.

Such binding reactions can be carried out (1) prior to fabrication of the film, while the polyurethane or urethane prepolymer are in solution (subsequent to the addition of the crosslinking or curing agent), or (2) after fabrication of the film.

In the first case, the biocide binding reaction would take place with the polyurethane in solution. In the second case, the biocide binding reaction would take place in the swelled network of the rubber. In both cases, the solvent or swelling agent must remain inert during the binding reaction.

After reaction, the solvent or swelling agent is removed as described in sections (1) or (3). Even though the biocide is chemically bound to the polyurethane chains, it will still phase separate in the rubber matrix, but on a much finer scale is than with the method described in section (3).

The necessity of using solvents or swelling agents may be obviated by employing water based synthetics.

(5) Sealing of Film Surfaces

For all the above methods, application of a final coating to seal the surfaces of the film to prevent leaching of the biocide during use or storage is highly desirable. Such a coating can be applied by a final dip in a polyurethane solution of low viscosity (low % solids), or by plasma or vapor deposition of a thin elastic polymer film.

Admixing of Gentian Violet with Latex

According to one aspect of the invention, gentian violet is admixed with liquid latex prior to membrane formation by dipping or spraying techniques. A wide variety of different concentrations may be used, but a 1.5% by weight solution of gentian violet is preferred. Applicant has found, that in addition to biocidal properties, the addition of gentian violet by admixing yields two unexpected results. The gentian violet appears to bind protein molecules in the latex, which yields two important benefits. First, this produces an anti-aging or anti-oxidizing effect which extends shelf life and increases tear resistance. Second, it appears to minimize allergic reactions in latex-allergic or sensitive users. Other proteing binding biocides may be employed in place of or in combination with gentian violet.

Microfiber Reinforcement

The present invention also contemplates membrane reinforcement by the addition of microfibers during the production process. Microfibers such as aramids, Kevlar, fiber glass, natural fibers, nylon, and graphite may be directly admixed with latex or polymer membrane materials either prior to, during, or after application. Such fiber reinforcement may be employed in connection with a single layer membrane, or in one or more layers of a multi-layer membrane. Fiber reinforcement may also be effected by adding one or more preformed sheet layers in a multi-layer membrane.

Reinforcement might also be employed by the incorporation of monofilament, similar to fishing line, in or between one or more layers, or by winding monofilament in a predetermined pattern around or between one or more layers.

Fish scale-like particles or small discs might also be employed to enhance strength and penetration resistance of membranes. Such scales or discs might be incorporated into or disposed between one or more layers of a single or multiple layer membrane. The scales or discs might also include magnetic properties such that they could be oriented in a predetermined manner by application of an electromagnetic or magnetic field during membrane formation.

List of Biocides That Applicants Believe Are Suitable for use in Connection with the Disclosed Invention Taken From A Book Entitled CTFA Cosmetic Ingredient Dictionary, 3rd edition, 1982. Published by The Cosmetic, Toiletry and Fragrance Association. Inc., Washington. D.C.

HC BLUE NO. 1
 $N^4$, $N^4$-Bls (2-Hydroxyethyl) -$N^1$-Methyl-2-Nitro-p-Phenylenedlamine
HC BLUE NO. 2
 $N^1$, $N^4$, $N^4$-(2-Hydroxyethyl)-2-Nitro-p-Phenylenediamine
HC BLUE NO. 3
 Cibalan Blue FBL
HC BLUE NO. 4
HC BLUE NO. 5
HC BROWN NO. 1
 Capracyl Brown 2R
HC ORANGE NO. 1
 2-Nitro-4-Hydroxydiphenylamine
HC RED NO. 1
 4-Amino-2-Nitrodiphenylamine
HC RED NO. 3
 $N^1$-(2-Hydroxyethyl)-2-Nitro-p-Phenylenediamine
HC RED NO. 6
HC YELLOW NO. 2
 N-(2-Hydroxyethyl)-2-Nitroaniline
HC YELLOW NO. 3
 $N^1$-Tris (Hydroxymethyl)-Methyl-4-Nitro-o-Phenylenediamine
HC YELLOW NO. 5
 $N^1$-(2-Hydroxyethyl)-4-Nitro-o-Phenylenediamine
NONOXYNOL-2
 Polyoxyethylene (2) Nonyl Phenyl Ether
NONOXYNOL-4, -8
NONOXYNOL-9 IODINE
NONOXYNOL-12 IODINE
PIGMENT RED 57
PIGMENT RED 57:1
PIGMNT RED 63:1
PIGMENT RED 64:1
PIGMENT RED 112
PIGMENT VIOLET 19
PIGMENT YELLOW 1
PIGMENT YELLOW 3
PIGMENT YELLOW 12
PIGMENT YELLOW 13
PIGMENT YELLOW 73
QUINOLINE
QUINOLINE SALTS
TERPENES
TERPINEOL
VAT DYES
XANTHENE
ACID BLACK 58
 Irgalan Grey B1
ACID BLACK 107
 Lanamid Black Bl.
ACID BLACK 131
 Nigrosine
ACID BLUE 9 AMMONIUM SALT
ACID BLUE 62
ACID BROWN 46
ACID BROWN 48
ACID DYES
ACID FUCHSIN
ACID GREEN 25
ACID ORANGE 7
ACID ORANGE 24
ACID RED 33
ACID RED 35
ACID RED 51
ACID RED 52
ACID RED 87
ACID RED 92
ACID RED 95
ACID VIOLET 43
ACID YELLOW 1
ACID YELLOW 3
ACID YELLOW 23
ACID YELLOW 73
ACID YELLOW 73 SODIUM SALT
D & C BLUE NO. 1 ALUMINUM LAKE
 Brilliant Blue Lake
D & C BLUE NO. 2 ALUMINUM LAKE
 Acid Blue 74, Indigetine 1A, Indigo Carmine
D & C BLUE NO. 4
 Acid Blue 9 (Ammonium Salt)
D & C BLUE NO. 6
 Indigo
D & C BROWN 1
 Resorcin Brown, Capracyl Brown
D & C GREEN NO. 3
 Aluminum Lake. Food Green 3
D & C GREEN NO. 5
 Acid Green 25
D & C GREEN NO. 6
 Solvent Green 3
D & C GREEN NO. 8
 Solvent Green 7
D & C ORANGE NO. 4
 Acid Orange 7
D & C ORANGE NO. 5
 Acid Orange 11. Solvent Red 72. Dibromofluorescein
D & C ORANGE NO. 5. ALUMINUM LAKE
 Dawn Orange. Manchu Orange.
D & C ORANGE NO. 5 ZIRCONIUM LAKE
 Petite Orange. Dawn Orange. Acid Red 26. Ponceau R.
D & C ORANGE NO. 10
 Solvent 73. Dilodofluorescein.
D & C ORANGE NO. 10 ALUMINUM LAKE
 Solvent Red 73. Erythrosine G.
D & C ORANGE No. 11

D & C ORANGE NO. 17
D & C ORANGE NO. 17 LAKE
D & C RED NO. 2 ALUMINUM LAKE
D & C RED NO. 3 ALUMINUM LAKE
D & C RED NO. 4 ALUMINUM LAKE
D & C RED NO. 6
   Lithol Rubin B
D & C RED NO. 6 ALUMINUM LAKE
D & C RED NO. 6 BARIUM LAKE
D & C RED NO. 7 CALCIUM LAKE
D & C RED NO. 7 ZIRCONIUM LAKE
D & C RED NO. 8
D & C RED NO. 8 BARIUM LAKE
D & C RED NO. 8 SODIUM LAKE
D & C RED NO. 9
D & C RED NO. 9 BARIUM LAKE
D & C RED NO. 9 ZIRCONIUM STRONTHIUM LAKE
D & C RED NO. 10
D & C RED NO. 17
D & C RED NO. 19
   Rhodamine B. Magenta
D & C RED NO. 19 BARIUM LAKE
   Rhodamine B. Magenta
D & C RED NO. 19 ZIRCONIUM LAKE
D & C RED NO. 21
D & C RED NO. 21 ALUMINUM LAKE
D & C RED NO. 21 ZIRCONIUM LAKE
D & C RED NO. 22
   Eosine YS
D & C RED NO. 27
D & C RED NO. 27 ALUMINUM LAKE
   Terabromo Terachloro Fluorescein Lake
D & C RED NO. 27 BARIUM LAKE
D & C RED NO. 27 ZIRCONIUM LAKE
D & C RED NO. 28
   Phloxine B
D & C RED NO. 30
D & C RED NO. 30 ALUMINUM LAKE
D & C RED NO. 30 CALCIUM LAKE
D & C RED NO. 31
D & C RED NO. 31 CALCIUM LAKE
D & C RED NO. 33
D & C RED NO. 34
D & C RED NO. 34 CALCIUM LAKE
D & C RED NO. 36
D & C RED NO. 36 BARIUM LAKE
D & C RED NO. 36 LAKE
   Chlorinated Para Lake. Tange Orange
D & C RED NO. 36 ZIRCONIUM LAKE
D & C RED NO. 37
   Rhodamine B-Stearate
D & C RED NO. 37 CALCIUM LAKE
   Rhodamine B. Stearate Solvent
D & C RED NO. 39
D & C RED NO. 40
D & C YELLOW NO. 5 ALLUMINUM LAKE
D & C YELLOW NO. 5 ZIRCONIUM LAKE
D & C YELLOW NO. 6 ALUMINUM LAKE
D & C YELLOW NO. 7
D & C YELLOW NO. 8
   Uranine, Sodium Fluorescein, Naphthol Yellow S
D & C YELLOW NO. 10
D & C YELLOW NO. 10 ALUMINUM LAKE
D & C YELLOW NO. 11
EXT. D & C VIOLET NO. 2
EXT. D & C YELLOW NO. 7
EXT. D & C YELLOW NO. 7 ALUMINUM LAKE
FD & C RED NO. 20
FD & C RED NO. 22
FD & C RED NO. 40
FD & C YELLOW NO. 5
FD & C YELLOW NO. 5 ALUMINUM LAKE
FD & C YELLOW NO. 6
FD & C YELLOW NO. 6 ALUMINUM LAKE
SOLVENT RED 48
SOLVENT RED 49:1
SOLVENT RED 72
SOLVENT RED 73
SOLVENT VIOLET 13
SOLVENT YELLOW 13
TARTRAZINE    Taken From "FEDERAL REGISTER", Vol. 43, No. 4—Friday, Jan. 26, 1978

Antimicrobial Soaps:
   Cloflucarban
   Para-chloro-mein-xylenof
   Povidone-iodine complex
   1.5 percent phenol or less aqueous/alcoholic
   Triclocarbon
   Triclosan
Health-care Peronnel Handwash
   Benzalkonium chloride
   Benzethonium chloride
   Clofluearban
   Hexylesorinal
   Iodine complexed with phophate eater of alkyaryloxy polyethlene glycol
   Methyl-benzethonium chloride
   Nonyl phenoxypoly (ethyleneoxy) ethanol-iodine
   Para-chloro-meta-xylenol
   Povidene-iodine complex
   1.5 percent phenol or less aqueous/alcoholic
   Poloxamer-iodine complex
   Tricloearban
   Undecoylium chloride-iodine complex
Patient Preoperative Skin Preparation
   Bonzalkonium chloride
   Benzethonium chloride
   Hexylresorcinol
   Iodine complexed with phosphate ester of alkylaryloxy polyethylene glycol
   Methylbenxethonium chloride
   Nonyl phenoxypoly (ethyleneoxy) ethanoilodine
   Para-thloro-meta-xylenol
   1.5 percent phenol or less aqueous/alcoholic
   Poloxamer-iodine complex
   Povidene-iodine complex
   Undecoylium chloride-iodine complex
Skin Antiseptic
   Benzalkonium chloride
   Benzathonium chloride
   Hexylresorcinoi
   Iodine complexed with phosphate ester of alkylaryloxy polyethylene glycol
   Iodine tincture
   Methyl-bonzethonium chloride Nonyl phenoxypoly (ethylencoxy) ethanoliodine
Para-chloro-meta-xylenol
1.5 percent phenol or less aqueous/alcoholic
Poloxamer-iodine complex
Povidene-iodine complex
Triclosan
Triple Dye
Undeseylium chloride-iodine complex Skin Wound Cleanser
  Cloflutarban
  Iodine complexed with phosphate ester of alkylaryloxy polyethylene glycol
  Iodine tincture
  Nonyl phenoxypoly (ethyleneoxy) ethanoliodine
  Para-chloro-meta-xylenol
  1.5 percent phenol or less aqueous/alcoholic
  Poloxamer-iodine complex
  Povidene-iodine complex
  Tricloearban
  Triclosan
  Undecoylium chloride-iodine complex Skin Wound Protectant
  Benzalkonium chloride
  Benzathonium chloride
  Hexylresorcinoi
  Iodine complexed with phosphate ester of alkylaryloxy polyethylene glycol
  Iodine tincture
  Methyl-bonzethonium chloride
  Nonyl phenoxypoly (ethylencoxy) ethanoliodine
  Para-chloro-meta-xylenol

We claim:

1. A latex article having a biocide barrier comprising:
a first layer consisting essentially of cured liquid latex and substantially free of biocide;
a second layer consisting essentially of a biocide effective as a coagulant for liquid latex, said second layer coating said first layer;
a third layer consisting essentially of a cured liquid latex and substantially free of biocide, said third layer coating said second layer wherein said second layer is at least partially bonded to said first layer and said third layer.

2. The latex article according to claim 1, wherein:
said third layer is thicker than said first layer.

3. The latex article according to claim 1, wherein:
said biocide of said second layer has a concentration of 0.10 to 5 percent by weight.

4. The latex article according to claim 1, wherein:
said biocide is selected form chlorhexidine, dextran sulfate, triclosan, benzalkonium, betadyne, gentian violet, acriflavine and acridine dyes, mercurochrome, silver salts, and an extract of blue-green algae.

5. The latex article according to claim 1, wherein:
said second layer has a weight ratio to said first layer of 0.05 to 0.3.

6. The latex article according to claim 1, wherein:
said second layer has a weight ratio to said third layer of 0.05 to 0.3.

7. The latex article according to claim 1, wherein:
said latex article is selected from the group of gloves, condoms, diaphragms, slippers, overshoes, sterile bands, catheters, tubings, drapes, gut openings, mouthpieces, nipples, intra gastric nasal tubes, kidney shunts, dams for teeth, braces for teeth, sub-clavian vein and artery shunts, and colostomy bags.

8. The latex article according to claim 1, wherein said first and third layers are discrete.

9. The latex article according to claim 1, wherein said article comprises a glove.

10. The latex article according to claim 1, wherein said article comprises a condom.

11. The latex article according to claim 1, further comprising a substance selected from the group consisting of sealants, biocides, indicators, spermicides, antiseptics, gels, hydrogels, pituitous substances, cleansing agents, surfactants, detergents, abrasives, coating agents, wiping agents, fibers, tactile enhancing objects, needle treating materials, tactile enhancing liquids, tactile enhancing gels, lubricants, and sheet forming agents, substantially contained between said first and third layers.

12. The article according to claim 1, further comprising an indicator operably associated with said article for providing to a user an indication of the presence of a pathogen.

13. The article according to claim 1, further comprising an indicator operably associated with said article for providing to a user an indication of membrane breach.

14. The article according to claim 1, further comprising a substance disposed and substantially contained between said first and third layers, said substance effective to contact and at least partially treat a needle or other instrument breaching at least one of said layers.

* * * * *